US00PP25858P3

(12) United States Plant Patent
Mazzardis

(10) Patent No.: US PP25,858 P3
(45) Date of Patent: Sep. 8, 2015

(54) BLUEBERRY PLANT 'EB 8-42'

(50) Latin Name: ***Vaccinium* Hybrid**
Varietal Denomination: EB 8-42

(71) Applicant: Vincent David Mazzardis, Joondalup (AU)

(72) Inventor: Vincent David Mazzardis, Joondalup (AU)

(73) Assignee: PRUNUS PERSICA PTY LTD, Joondalup (AU)

( * ) Notice: Subject to any disclaimer, the term of this patent is extended or adjusted under 35 U.S.C. 154(b) by 156 days.

(21) Appl. No.: 13/986,862

(22) Filed: Jun. 12, 2013

(65) Prior Publication Data

US 2013/0340130 P1 Dec. 19, 2013

(51) Int. Cl.
*A01H 5/00* (2006.01)
*A01H 5/08* (2006.01)

(52) U.S. Cl.
USPC ..... Plt./157
CPC ..... *A01H 5/08* (2013.01)

(58) Field of Classification Search
USPC ..... Plt./157
See application file for complete search history.

(56) References Cited

FOREIGN PATENT DOCUMENTS

AU 2012/113 6/2012

*Primary Examiner* — Annette Para
(74) *Attorney, Agent, or Firm* — Paine Hamblen, LLP

(57) ABSTRACT

A new and distinct variety of blueberry plant, which is denominated varietally hereinafter as 'EB 8-42' is described, and which further produces an attractively colored, large fruit, which is mature for harvesting and shipment in the early season under the ecological conditions prevailing in Yanchep, Western Australia.

1 Drawing Sheet

Latin name: '*Vaccinium* Hybrid'.
Varietal denomination: 'EB 8-42'.
Related Application Data
The present application claims priority to Australian Plant Breeders Rights Application Serial No. 2012/113, and which was filed on 14 Jun. 2012.

BACKGROUND OF THE NEW VARIETY

The present invention relates to a new novel and distinct variety of blueberry plant '*Vaccinium* Hybrid,' and which has been denominated varietally, hereinafter, as 'EB 8-42'.

ORIGIN AND ASEXUAL REPRODUCTION

The present variety of blueberry plant resulted from an ongoing plant development program which has been conducted by me at my farm which is located in Yanchep Springs, in Yanchep, Western Australia. The new variety of blueberry plant was derived from a controlled cross-pollination conducted by me and made in 2005. The controlled pollination included the seed parent, blueberry plant '03-2' [unpatented], and the pollen parent which was the blueberry plant named 'SB-1' [also unpatented]. This cross-pollination took place in Yanchep Springs, Western Australia. The seed parent, blueberry plan '03-2' is characterized by a semi-upright bush type growth pattern, and further displays mid-season flowering, and additionally produces medium to large sized fruit. The pollen parent, blueberry plant 'SB-1' is characterized by a semi-upright growth pattern, large, firm fruit, and further has an early season of flowering. Seed derived from the '03-2' blueberry plant [unpatented] produced approximately 500 plants. The first fruit produced from this first controlled pollination were seen and evaluated in 2007. The fruit and the growth habit of the new variety were then studied at that time. A further assessment took place during the 2008 growing season, and the new variety 'EB 8-42' was then selected for further study and asexual propagation. The present variety 'EB 8-42' was asexually reproduced by cuttings during the 2009 to 2012 growing seasons. Progeny produced from this asexual reproduction were continuously observed, and it has been determined since that time that the new variety, 'EB 8-42' is a distinct and novel variety of blueberry plant. The present variety of blueberry plant is noteworthy for producing extra large sized fruit which is very firm. Still further, the variety and the fruit thereof has a small, dry picking scar and a good fruit flavor, as well as early flowering and fruit production dates.

In relative comparison to the seed parent, blueberry plant '03-2,' the new blueberry variety has an earlier date of fruit maturity than that of the blueberry plant '03-2,' which is considered to be mid to late season. Additionally, in relative comparison to the blueberry plant '03-2,' the fruit produced by the new variety of blueberry is considered large to very large as compared to the parent, which is only medium in size. Additionally, the new variety has a growth habit different from the seed parent, that being '03-2', by producing a semi-upright growth habit as opposed to the spreading growth habit that the seed parent normally displays. Still further, the present variety produces fruit, having a round shape in contrast to the fruit shape of the seed parent, that being '03-2,' which is globose. In relative comparison to the pollen parent 'SB-1,' the fruit maturity, size, growth habit and fruit shape are all different from the pollen parent 'SB-1.' Again, the pollen parent matures in the mid to late season, has a medium fruit size, a spreading growth habit, and produces a fruit with a globose shape. On the other hand, the new variety of blueberry plant has an early date of fruit maturity, has a large to very large fruit size, a semi-upright growth habit, and a round, fruit shape.

BRIEF DESCRIPTION OF THE DRAWING

The accompanying drawing, which is provided, is a color photograph of the new blueberry plant.

FIG. 1 depicts several mature berries sufficiently matured for harvesting and shipment. Several leaves are depicted showing the dorsal and ventral coloration, and a vegetative shoot is shown which illustrates the growth habit of the new variety of blueberry plant. Still further, the present drawing includes a photograph illustrating a representative vegetative shoot and several leaves, and the fruit produced by the 'Sharpeblue' blueberry plant, which is the closest known variety to the present new blueberry plant.

The colors in this photograph are as nearly true as is reasonably possible in a color representation of this type, due to chemical development, processing and printing, the leaves and fruit depicted in this photograph may or may not be accurate when compared to the actual specimen. For this reason, future color references should be made to the color plates provided in The Royal Horticulture Society Colour Chart ($5^{th}$ Edition), and other color descriptions provided hereinafter.

NOT A COMMERCIAL WARRANTY

The following detailed description has been prepared to solely comply with the provisions of 35 U.S.C. §112, and does not constitute a commercial warranty (either expressed or implied), that the present variety will, in the future, display the botanical, horticultural or other characteristics as set forth, hereinafter. Therefore, this disclosure may not be relied upon to support any future legal claims including, but not limited to, breach of warranty of merchantability, or fitness for any particular purpose, or non-infringement, which is directed, in whole, or in part, to the present new variety.

DETAILED DESCRIPTION

Referring more specifically to the botanical and horticultural details of this new and distinct variety of blueberry plant, the following has been observed during the sixth fruiting season, under the ecological conditions prevailing at the farm of the inventor, which is located in the town of Yanchep Springs in Yanchep, Western Australia. Common color names are occasionally used.

PLANT

Plant vigor: Generally considered medium to strong for the species.

Plant growth habit: Generally speaking, semi-upright. This is in contrast to the closest known variety, which is the 'Sharpeblue' blueberry plant [unpatented], and which has an upright growth pattern.

Plant size: 1.5 meters in height, and about 1.2 meters in width.

One year old shoots:

*Color.*—Yellow-Green, (RHS 138B).

One year old shoots:

*Internode length.*—Considered short to medium in length. This is in contrast to the internode length as displayed by the 'Sharpeblue' blueberry plant, where the internode length is considered medium to long for the species.

LEAF

Leaf length: Considered to be short to average in length relative to other species, about 58 mm. This is in contrast to the closest known variety, which displays a leaf length which is considered medium to long for the species.

Leaf width: Considered narrow to medium in width, about 24 mm. This is in contrast to the leaf width as seen in the drawing for the 'Sharpeblue' blueberry plant, whose leaves are considered medium to broad. The different leaf lengths and widths of the new variety as compared against the closest known variety are best seen in FIG. 1.

Leaf:

*Ratio to length/width.*—Considered large for the species. This is in contrast to the same ratio of length/width of the leaves as provided by the 'Sharpeblue' blueberry plant, which are considered medium to large in size. Please see FIG. 1.

Leaf shape: Considered ovate.

Leaf color:

*Dorsal surface.*—Green, (RHS 133A).

Leaf color intensity:

*Dorsal surface color intensity.*—Yellow-green (RHS 148C). This is in contrast to the same characteristic as displayed by the leaves of the 'Sharpeblue' blueberry plant where the dorsal surface color intensity is considered a light to medium green.

Leaf margin: Considered entire.

Flower bud coloration: Very weak anthocyanin coloration is present.

Inflorescence:

*Length.*—Considered medium to long, about 13 mm. This is in contrast to the closest known variety, the 'Sharpeblue' blueberry plant, and which has an inflorescence length, which is only considered average for the variety.

*Average flower width.*—About 7 mm.

Flower size:

*Corolla.*—Considered average for the species. This is in contrast to the same characteristic as displayed by the 'Sharpeblue' blueberry plant where the same plant feature is considered to be medium to large.

Open flower color: White (RHS NN 155D).

Corolla tube coloration: A very weak to weak anthocyanin coloration is displayed. The closest known variety, the 'Sharpeblue' blueberry plant, displays a similar characteristic which is only considered weak.

Corolla length: About 9 mm.

Flower:

*Ridges.*—Generally speaking no ridges are detected on the corolla tube for the new variety. However, ridges do appear on the closest known variety, that being the 'Sharpeblue' blueberry plant.

Fruit cluster density:

*Generally.*—Considered dense. This is in contrast to the same characteristic as displayed by the 'Sharpeblue' blueberry plant where the fruit density is considered dense to very dense.

Unripe fruit color intensity: Considered average for the new variety, Yellow-Green (RHS 145A). This is in contrast to the light to medium green color as found in the fruit produced by the 'Sharpeblue' blueberry plant, and which is the closest known variety.

Fruit size:

*Generally.*—Considered large for the species, about 19 mm. This is in contrast to the fruit size produced by the 'Sharpeblue' blueberry plant, which is only considered medium for the species.

Fruit shape:

*Generally.*—When viewed in a longitudinal sectional plane, the fruit has an oblate shape.

Sepal orientation: Considered semi-erect. This is in contrast to the closest known variety, the 'Sharpeblue' blueberry plant, where the sepal orientation is considered to be erect.

Sepal form:

*Generally.*—Incurving. This is in contrast to the closest known variety where the sepal form is considered to be straight.

Calyx basin:

*Diameter.*—Considered medium to large for the species, and having a diameter of about 6.1 mm. This is in contrast to the fruit produced by the 'Sharpeblue' blueberry plant where the calyx basin diameter is considered small to medium for the variety.

Calyx basin depth: Considered average to deep, about 2 mm. This is in contrast to the closest known variety, the 'Sharpeblue' blueberry plant, and which is considered average for the species.

Intensity of bloom:

*Generally.*—The present variety has very strong bloom intensity. This is a greater bloom intensity than the strong bloom intensity as displayed by the 'Sharpeblue' blueberry plant, which is the closest known variety.

Fruit skin color:

*Generally.*—Considered to be dark blue (RHS 103A).

Fruit firmness:

*Generally.*—Considered to be firm. This is in contrast to the fruit produced by the 'Sharpeblue' blueberry plant, where the fruit has a soft to medium fruit firmness.

Fruit flesh:

*Color.*—Yellow-Green (RHS 145C).

Fruit sweetness: Considered medium to high. This is greater than the fruit sweetness as typically displayed by the 'Sharpeblue' blueberry plant.

Color of seeds: Brown (RHS N 200A).

Fruit acidity:

*Generally.*—Considered low to medium. This is in contrast to the medium fruit acidity as typically displayed by the fruit of the 'Sharpeblue' blueberry plant, and which is the closest known variety.

Plant:

*Fruiting type.*—Present on one year old and current season shoots.

Vegetative bud burst: Generally speaking, the new variety is considered very early in the season, and earlier in time than the vegetative bud burst as displayed by the 'Sharpeblue' blueberry plant.

Flowering time:

*One year old shoots.*—Considered very early in the season and earlier in time than the flowering characteristics as displayed by the 'Sharpeblue' blueberry plant.

Flowering time:

*Current year's shoots.*—Considered very early in the season, and earlier in time than that displayed by the "Sharpeblue" blueberry plant, which is the closest known variety.

Date of fruit ripening:

*One year old shoots.*—Considered very early. In relative comparison to the closest known variety, the ripening date is earlier in time to that which is displayed by the 'Sharpeblue' blueberry plant.

Date of ripening on current year's shoots: Considered very early in the season, and earlier in time than that which is displayed by the 'Sharpeblue' blueberry plant, and which is the closest known variety.

Resistance to insects and disease: No particular susceptibilities were noted. The present variety has not been tested to expose or detect any susceptibilities or resistances to any known plant and/or fruit diseases.

Although the new variety of blueberry plant possesses the described characteristics when grown under the ecological conditions prevailing near Yanchep Springs, Western Australia, it should be understood that variations of the usual magnitude and characteristics incident to changes in growing conditions, fertilization, pruning, pest control, frost, climatic variables and horticultural management are to be expected.

Having thus described and illustrated my new variety of blueberry plant, what I claim is new and desire to secure by Plant Letters Patent is:

1. A new and distinct variety of blueberry plant, substantially as illustrated and described, and which is characterized principally as to novelty by producing an attractively colored and large fruit, which is mature for harvesting and shipment early in the season, and under the ecological conditions prevailing in Yanchep, Western Australia.

* * * * *

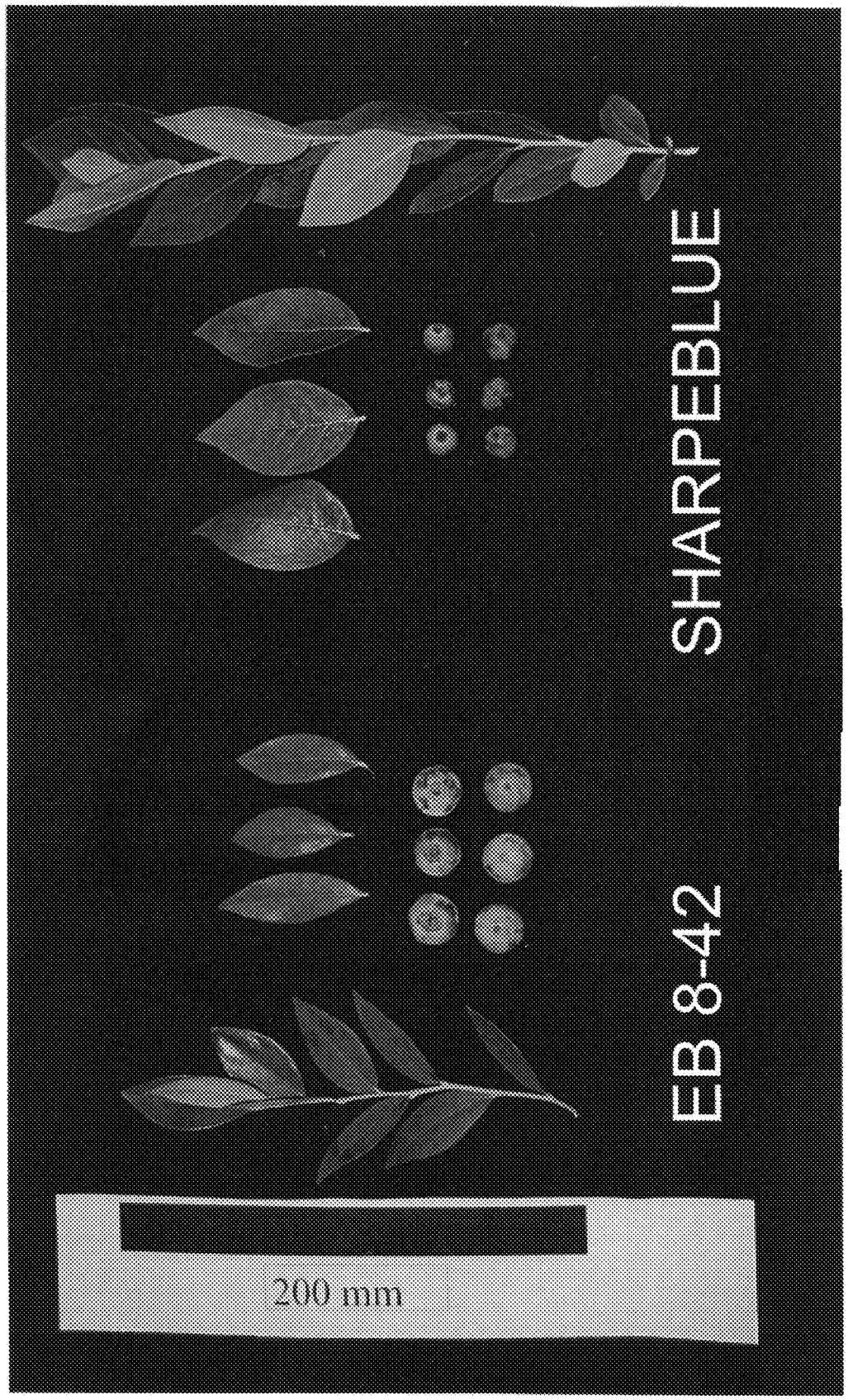
EB 8-42
SHARPEBLUE
200 mm